US007575555B1

(12) United States Patent
Bryant

(10) Patent No.: US 7,575,555 B1
(45) Date of Patent: Aug. 18, 2009

(54) DOCKING STATION FOR RETRIEVING DATA IN CONJUNCTION WITH IMPROVED INCENTIVE SPIROMETRY DEVICES

(76) Inventor: Terry Keith Bryant, 1281 E. Blue Heron Blvd., Singer Island, FL (US) 33404

( * ) Notice: Subject to any disclaimer, the term of this patent is extended or adjusted under 35 U.S.C. 154(b) by 0 days.

(21) Appl. No.: 11/421,976

(22) Filed: Jun. 2, 2006

Related U.S. Application Data

(63) Continuation-in-part of application No. 11/188,469, filed on Jul. 25, 2005, which is a continuation-in-part of application No. 10/810,876, filed on Mar. 26, 2004, now Pat. No. 6,942,625.

(60) Provisional application No. 60/458,176, filed on Mar. 27, 2003, provisional application No. 60/379,908, filed on May 11, 2002.

(51) Int. Cl.
*A61B 5/08* (2006.01)
(52) U.S. Cl. ..................... 600/538; 600/529
(58) Field of Classification Search ......... 600/529–543, 600/300, 301
See application file for complete search history.

(56) References Cited

U.S. PATENT DOCUMENTS 6,126,613 A * 10/2000 Edwards et al. ............ 600/539
6,190,326 B1 * 2/2001 McKinnon et al. .......... 600/529
6,398,727 B1 * 6/2002 Bui et al. ................... 600/300
6,579,242 B2 * 6/2003 Bui et al. ................... 600/537
6,656,129 B2 * 12/2003 Niles et al. ................. 600/540
6,662,032 B1 * 12/2003 Gavish et al. .............. 600/323
6,733,464 B2 * 5/2004 Olbrich et al. ............. 600/538
2003/0050537 A1 * 3/2003 Wessel ...................... 600/300

* cited by examiner

*Primary Examiner*—Robert L. Nasser, Jr.
*Assistant Examiner*—Navin Natnithithadha
(74) *Attorney, Agent, or Firm*—Daniel S. Polley, P.A.

(57) ABSTRACT

An apparatus used in the medical industry, in order to increase transpulmonary pressure and respiratory volumes, to improve inspiratory muscle performance and re-establish the normal pulmonary hyperinflation, through the employment of electronic technology, providing audible, simulated, verbal, human sounding words, that assist, guide and prompt, increasing patient usage. In the past, lack of usage of this simple plastic, antiquated, disposable unit, by the patient, has contributed to severe problems, such as pneumonia. Without prompting, the patient finds it hard to inhale into a tube repetitively, to improve their lungs. Previous applications of prior equipment has been poor, thus adding intelligence in the form of electronic technology, which prompts without assistance, is a tremendous advantage in helping not only the sighted, but also the blind as well, since normally only written information accompanies the incentive spirometer, thus, changing the use of this medical device as we know it today.

9 Claims, 7 Drawing Sheets

Present Invention Within Housing of Medical Apparatus

Fig. 1  Present Invention Within Housing of Medical Apparatus

*Fig. 2* Present Invention Within Housing of Medical Apparatus

Fig. 3    Perferred Embodiment of Spirometer Gauge 2

Fig. 4  Present Invention Within Housing of Gauged Spirometer 16

Fig. 5    Perferred Embodiment of Deactivation Key for Present Invention Within Housing of Medical Apparatus

DOCKING STATION FOR RETRIEVING DATA IN CONJUNCTION WITH IMPROVED INCENTIVE SPIROMETRY DEVICES

This application is a continuation-in-part of U.S. application Ser. No. 11/188,469, filed Jul. 25, 2005, which is a continuation-in-part of U.S. application Ser. No. 10/810,876, filed Mar. 26, 2004 and also claims the benefit of and priority to U.S. Patent Application Nos. 60/458,176, filed Apr. 11, 2003 and 60/379,908, filed Mar. 27, 2003. All of the above applications are incorporated by reference in their entireties.

BACKGROUND OF THE INVENTION

The present invention relates to enhancement of the Incentive Spirometer Medical Apparatus, a plastic disposable device, through electronic technology within the medical apparatus itself which is normally used to help in the rehabilitation of the lungs after an operation or similar type situations. The Incentive Spirometer consists of a plastic bell jar with a float inside the bell that rises, due to air being inhaled through a tube that is attached to the bell jar. By inhaling in the tube, the patient attempts to reach different volumes that are represented on the bell jar, where the float is used as a measuring device, but the float in the bell jar moves slowly and does not remain at it's apogee for very long, making visual accuracy for reading it's measurements on the scale, (on the bell jar), difficult especially since it is a repetitive inhalation process. The purpose of this prior art, is to bring air into the patient's lungs. The more air and use of the device, the better the patient's lungs become and thus the lungs are strengthened, however as recent studies have shown, complications such as pneumonia occur, are due to the lack of compliance, by the patient. Normally, the patient must utilize this medical apparatus without ancillary medical assistance and is expected to basically read written information on how to use the device, which is often performed improperly. Prior art required the patient to do the therapy unsupervised. The present invention overcomes the problems with the prior art and provides audible, verbal commands, encouraging phrases, responses, promptings and guidance electronically, allowing not only the sighted but the blind to benefit as well, providing a new method of technology in the medical industry.

SUMMARY OF THE INVENTION

The present invention relates to improving upon a disposable apparatus used in the medical industry, in order to increase transpulmonary pressure and respiratory volumes, improve inspiratory muscle performance, and re-establish the normal pulmonary hyperinflation, utilizing the employment of an audible, verbal, simulated vocalization of a humanlike voice through the use of modern technology, or any process available to accomplish this employment. Since, repeated usage of said medical apparatus on a regular basis allows airway passages to be maintained and lung atelectasis to be prevented or reversed. This new invention will prompt and encourage the patient, through the employment of an audible, verbal, simulated, generated, synthesized, or any similar process that can provide the function to produce humanlike voice, voices, word, words, or phrases, in order to help motivate the patient to use said apparatus and fulfill the recommended therapeutic sessions.

To achieve the function provided by the present invention, as described herein, and being that there are many different components presently available that can be used to facilitate the completion, operation, or function of the present invention, some examples of possible components are: micro chips, micro controllers, intregated circuit controllers, coin cells, power sources, batteries of a variety of sizes, (rechargeable or non-rechargeable), power adapters for direct current power supply for whatever requirements in relationship to any existing country, multiplexor circuits, electrodes, mylar speakers, sound modules, inductors, electro chromium, PC boards, inductive sensory systems, electrolyte layers, voltage regulators, oscillators, or indicators, just to name a few, however, not limited to and the exact components or combination of components will not be described specifically, except when applicable to context in order to simplify the specifications necessary to accomplish, or achieve the concept of the function of the present invention.

The present invention encompasses the entirety of the necessary components for the conception, as herein specified, of the above said medical apparatus, subject to patent allowance, in relationship to the utilization of present, future, new or impending technology, to create the same effect, as described herein as applies to the function of said apparatus, in order to produce audible, verbal, simulated, generated, or prerecorded humanlike voices phrases, or any similar method of providing the same effect, that will supply verbal commands, or responses to the patient, as specified herein.

The present invention encompasses the use of humanlike voices, in which a single word, words, or phrases, are produced through the components required for function, as herein stated, whether simulated, generated, prerecorded, synthesized, artificially produced, or any similar process, or combination of components imperative in order to supply the necessary function to facilitate the appropriate use of the present invention, as specified herein, in order to supply a verbal vocalization of a humanlike voice. The function of the present invention, to provide a humanlike voice or sound of an audible, verbal, humanlike word, words, or phrases, or any similar function.

The word humanlike does encompass the use of audible, verbal words, or phrases, or a single word that may sound different in a variety of tones, such as a talking or speaking animal, simulated or generated voices, or similar voice animation's, to produce a humanlike sound, as described herein, as animals do not normally speak. So, the variation of sound as specified in the present invention, when relating to the definition of humanlike, as herein pertains, is confined to the characteristic of an audible, verbal, simulated, generated, or synthesized words or a single word, as aforementioned, that sound like human words, encompassing any language in relationship to the function of the above said medical apparatus, as pertains to the present invention.

The word apparatus refers to the use of Incentive Spirometry devices as aforementioned in correlation with the concept of the function of the present invention and more specifically to the incentive spirometer, however not limited to, as with the function of the present invention other applications of the incentive spirometry may apply as deemed.

The word medical, as herein specified, relates to apparatus, or therapy in which the present invention is being employed, in order to benefit those conditions, or any specialized condition, in which the patient, person, or persons, using the prescribed therapy pertaining to the apparatus, through said use of said apparatus, can hopefully benefit.

The word patient, as herein specified, relates to any, person or persons, utilizing the above said medical apparatus, according to the system of therapy in which the medical apparatus applies in relationship to the present invention in regards to the specification to function as herein described, but not limited to.

The accepted name for the above mentioned medical apparatus, which usually only gives incentive to the patient through visual confirmation, is Incentive Spirometry device, also referred to as sustained maximal inspiration (SMI), which is a component of bronchial hygiene therapy. However, to simplify the conception and the specification of the field of the invention, the name of the present invention, which is the incentive spirometer, shall be known herein and referred to as, Lung Enhancer, which is the combination of any or all parts of whatever equipment or components are needed to provide the function of the present invention as herein mentioned and can also be used separately, utilizing it's own housing, supplying an audible, verbal, response without visual affirmation, as it does not require the housing of the above mentioned medical apparatus, should one desire to eliminate it. The Lung Enhancer can utilize voice chips or modules, as applicable, or any similar device, which in combination, can produce, generate, or synthesize, however, not limited to these exact components in order to provide a humanlike voice, word, words or phrases which will give an audible, verbal response or command to the patient, so the patient may obtain the particular goal, predetermined flow rate, or volume of air needed to be inhaled.

When the Lung Enhancer is combined with the above said medical apparatus, or used separately, through the combination of the necessary components, as described herein, the operation of the said medical apparatus can be adjusted, according to the patients goals, to provide verbal responses, or commands, to the patient, in order to encourage usage. Since, utilizing the combination of those components necessary to facilitate the function of the Lung Enhancer, with the above said medical apparatus provides visual and audible incentive, it is obvious that the combination of the Lung Enhancer with the Incentive Spirometry Device, or said medical apparatus is more applicable for fulfilling the maximum functional purpose of the Lung Enhancer, and will be described herein pertaining to such, however, not limited to.

Thus, the main purpose of the above said, audible, verbal humanlike voice commands or responses as provided by the Lung Enhancer, is to give incentive to the patient in order to encourage the usage of the apparatus, to improve lung function, and correct the possible problems that may occur without proper therapy, as described herein. In order to provide the Lung Enhancer with the appropriate functions for the apparatus, a microcontroller, but not limited to, can be used to facilitate the different settings that the Lung Enhancer can supply in conjunction with the adequate components to provide an audible, verbal, simulated, generated, synthesized, or any similar process that can provide humanlike, words, or phrases, or a single word to the patient in order to encourage use of the apparatus. The target amount of inhaled volume can be set in the Lung Enhancer so that the patient must reach his or her initial volume prior to the next level of increasement needed, per the therapeutic requirements and the Lung Enhancer will automatically increase the increments of volume required for the patient's exercise, thus, the patient will be required to improve their performance and thus, improve their lungs and medical health.

With the above mentioned additional benefit, when the patient reaches his or her particular respiratory inhaled volume, an audible verbal response from the Lung Enhancer will give an immediate indication of whether the volume, volumes, points, ratios, or performances accomplished by the patient, or any similar goal, have been reached through the sound of an audible, verbal, humanlike, simulated, generated, synthesized, or any similar process that will produce a voice, or voices originating from the apparatus itself, by giving the exact measurement and helpful incentive, to encourage the patient to continue to use the apparatus, according to the aforementioned programmable functions. Should the attempted aforementioned programmable, therapeutic goals or volumes fail to be accomplished by the patient, the Lung Enhancer will provide an audible, verbal, simulated, or otherwise produced, as above mentioned, humanlike voice, or phrases which will confirm that the patient has not achieved their goals accordingly, and a corresponding audible, verbal vocalization, as described herein, such as, "try harder" but not limited to, will inform the patient of their particular progress, output, or momentum through a humanlike voice originating from the apparatus itself, as herein described. However, this is not a required addition to the apparatus, but it is covered as part of the invention, in relationship to exploiting the fullness of the complete functional operation of the apparatus, so as to provide the most advantageous benefit to the patient through providing a gauge or similar device, in order to allow the patient to achieve adequate audible, verbal, verification of the patients pre-set goals or achievements.

On the other hand, the constructor of the apparatus may desire to avoid the additional cost of components necessary to produce the additional adjustable function and can be avoided if so desired, as the Lung Enhancer can be constructed to only coincide with the visual readings that normally exists on the above said medical apparatus and will solely provide only those exact readings being performed by the patient and the Lung Enhancer shall provide verification of those inhaled volumes, or readings through the audible, verbal, humanlike phrases, as described herein, without setting any goals, according to the construction of the apparatus. So, the constructor may choose to eliminate the use of allowing the patient to set his or her own settings accordingly. Whether constructing the apparatus with self gauging devices as aforementioned or simply allowing the Lung Enhancer to only audible or verbally speak the ratios or volumes or other readings inhaled by the patient without attempting to reach goals, as aforementioned, both functions allow the blind to benefit as well as the patient with sight, as the blind will be able to hear their inhaled volumes.

So, the construction of the above said apparatus is at the discretion of the constructor, and will be based on the function that one desires to fulfill utilizing the Lung Enhancer, A voice chip, or similar unit, constructed within the above mentioned Lung Enhancer can provide humanlike voice phrases that will allow the patient using it to inhale, while at the same time, an audible and verbal response will verify whether the person using the Lung Enhancer has reached their particular goals. This will be achieved through the use of a simulated, generated, synthesized, prerecorded human voice, or anything similar in order to facilitate function, as herein described, (male or female), which can be applied in combination with said apparatus, as aforementioned and the Lung Enhancer will prompt the patient through audible, verbal simulated words or a single word or phrase, to either, "try again", or "good job, you hit your mark", or "great", or any phrase similar, but not limited to, that applies accordingly, in relationship to the particular use that the Lung Enhancer requires at that time, in relationship to function, as described herein. Since, one must inhale to help facilitate the improvement of ones lung capacity and health, as described herein, an air pressure sensor, or similar device, can be installed at the appropriate location on the Lung Enhancer itself, to measure the exact amount of volume being inhaled and relay those accurate readings in synthesis to the appropriate components, in order to supply audible, verbal verification of said readings as mentioned herein, corresponding to the visual measurements being performed on the apparatus, in order to complete this function of the Lung Enhancer, encouraging or correcting the patient accordingly, with an audible, verbal, simulated humanlike voice, as aforementioned, to give verification of the amount of volume being produced.

The above said sensor can be placed at whatever location facilitates the function of the Lung Enhancer as mentioned herein, and should be connected directly to the area in which one is inhaling. Normally, a tube is used to inhale the amount of air the patient is bringing into the lungs, however, the new Lung Enhancer invention is not limited to the physical structure of any apparatus, that is providing the medical function as described herein. Should cost be a consideration, the Lung Enhancer invention can utilize electronic sensors (but not limited to), attached directly to the above said apparatus at each point, in which the air volume is normally visualized by a float which will relay electronic signals, but not limited to, allowing the constructor of the apparatus to eliminate the above said sensor while still allowing the concept of the facilitation of the function of the lung Enhancer, as herein described. This alternative appropriation of components to achieve the same function by eliminating the pressure sensor, as above stated, will still give the completeness of the necessary function as previously described in relationship to the medical apparatus, prompting the patient using the Lung Enhancer to accomplish the goals or requirements of that therapy, in compliance to the apparatus by employing audible, verbal, incentive utilizing simulated, generated, synthesized or any similar process in order to produce humanlike words, or phrases or a single word which encompasses the concept of the embodiment of the present invention, as herein described. A speaker can be attached to whatever housing, on the aforementioned apparatus, as needed to produce the requirement audible, verbal sound, as herein described and the Lung Enhancer can have as many audible verbal commands and responses, supplying simulated human voice as desired, according to the output potential employed by the construction of the above said apparatus. Said construction is not contained to any degree herein, as specific ratios and outputs will depend on the application and construction designed to promote the usage of the device and obviously some apparatus may require particular specialization's to provide the audible, verbal simulated human voices as aforementioned and the provider of the apparatus shall maintain the specifications or structure of each unit produced in which the new Lung Enhancer invention is utilized, under the SMI therapeutic requirements as aforementioned.

Another important benefit of the Lung Enhancer, is the ability to install a programmable timer for letting the person manipulating the device to know what time he or she should begin using the apparatus. The aforementioned programmable timer is not necessarily required to fulfill the concept of the Lung Enhancer, however, it is encompassed within the concept of the present invention, so as to achieve the fullness of the complete available functional operation of the apparatus according to the patient's particular need, or therapeutic program, which shall virtually be provided without the use of any assistance, as the normal therapeutic requirement, will be replaced by the use of an audible, verbal, simulated, generate, synthesized human voice, word, words, or phrases, or any similar process as described herein, and this function will be provided by the Lung Enhancer, which will automatically vocalize that it is time for the person or patient to use the apparatus as needed. This will assure the patient is diligent to continue the necessary procedure to increase respiratory rate as prescribed, as the Lung Enhancer can be adjusted to continue to provoke the patient, through audible, verbal, simulated human voices, phrases, and reminders that will continue to say audible, verbal, simulated human phrases giving incentive to help encourage the patient, until the patient uses the apparatus, to achieve the patients up-most potential. With a device as important as the aforementioned apparatus, the therapeutic recommended interval for usage of respiratory spirometry devices is normally 1 hour, under the SMI therapeutic requirements as aforementioned, the Lung Enhancer can provide the doctor or therapist with the ability to set the exact amount of time in correlation with the constructor in order to provide the appropriate functions, between each use so that the patient can be reminded accordingly at that time, through an audible, verbal humanlike reminder, as described herein, using a word or phrase to accomplish this recommended therapeutic utilization of the apparatus though the operation of an audible, verbal incentive emanating from within the apparatus itself. However, preferably the construction of the apparatus would be more advantageous by presetting the therapeutic time intervals prior to making the unit available to the patient, so that the patient cannot change the intervals on their own, thus, preventing any interruption of the therapeutic session required by the Lung Enhancer. This adjustment of therapeutic time intervals can be pre-set in the unit, so as to make the operation of the present invention as simple as possible and also prevent any tampering with the unit by unauthorized personnel.

Since the Lung Enhancer, will have a "nag" ability, which means a series of continuous verbal command which prompts the patient until the Lung Enhancer is used appropriately and will be programmed within the housing of the Lung Enhancer itself. The aforementioned "nag" program function of the present invention will give incentive for the patient to use it; such as an audible, verbal command saying, "pick the unit up", or verbal incentive coming directly from the Lung Enhancer itself, saying a phrase such as: "it is now time for the exercise program", but not limited to these exact commands. A sleep mode can be programmed in the Lung Enhancer, which will allow the Lung Enhancer to basically stop working, or take a break, or turn back on, to perform the appropriate function, such as when to begin the SMI therapeutic sessions again like, "time for your therapy", but not limited to, in order to save battery life and/or the power source and can be programmed within the housing of the Lung Enhancer. Another way of programming the Lung Enhance, to shut off or on, at any time and/or during the sleeping period of the patient, is by utilizing a card or key, but not limited to this exact principle, made of whatever material facilitates the function, on the apparatus itself, but not limited to, according to the construction per the constructor's design, at whatever location deemed necessary, to achieve said function and can be slid or slid out, to turn the unit on or off, but not limited to, by providing conductivity at the point of origin when inserted, and this shall be known herein as "slip chip". Removing the slip chip permanently, never allowing the conductivity to be resumed, would avoid any tampering of this most advantageous aspect of the slip chip which is the continuation of the therapeutic performance of the Lung Enhancer.

Another way of facilitating the turn off, turn on ability of the Lung Enhancer would be through the use of light photosensors installed in the unit itself, such as; 1PC81X (Daylight sensor), but not limited to this particular component, which shall perform the duties of turning off the Lung Enhancer during the night, by sensing the absence of light, (darkness), or lack of light and thus, turning the Lung Enhancer back on when light is present. With this in mind, the Lung Enhancer will continue to perform its operation and function throughout the day, or as constructed according to the requirements of the therapist and will allow the patient to sleep during the period when light is not sensed by the sensor in the Lung Enhancer. The embodiment and descriptions to follow, will use gauging of the Lung Enhancer, through the utilization of the float mechanism within the bell jar of the apparatus, in order to provide the most cost effective and advantageous method to perform the function of the present invention, with conductivity. With this in mind, one must have knowledge of the basic construction of the Incentive Spirometer to understand the electronic improvements and enhancements described herein.

With this understanding the Incentive Spirometer comprises of a plastic bell jar with a mechanical float, that rises due to air being inhaled by the person or patient through an attached tube. At the same time, the air (patient's breath), flowing out of the bell jar, when the apparatus is being used, causes the mechanical float in the bell jar to rise, such that the position of the float is relative to the volumetric pressure printed on the bell jar, which accurately reflects the amount of air inhaled. The float in the bell jar moves slowly but does not remain at it's apogee for very long and makes visual accuracy for reading its position measurements on the scale (on the bell jar), difficult. One application for allowing the float mechanism in the Lung Enhancer, is to relay the measurement of the float positioning in correlation, with the numerical positions on the bell jar cylinder, (which encompasses the float).

It is obvious that both the bell jar and the float must have conductive material on them, of whatever conductive material is appropriate to facilitate the function of the present invention, by whatever means is deemed by the constructor of the apparatus. A cylinder sensor strip within the housing of the unit, in correlation with the numerical measurements on the bell jar of the Lung Enhancer's housing, but not limited to, would allow the float and said conductive sensor strip, to adjacently touch, to relay correspondence to the appropriate components. To supply conductivity for said movable float, with the understanding that the preferred method of providing conductivity, for either of the above mentioned float, or conductive sensor strip, could be plating, but not limited to this exact way of supplying conductivity, each above said units with conductive materials such as aluminum, nickel, copper, or gold, or any conductive material that would facilitate the function of the present invention, can be used to relay the electric conducted signal, to the appropriate source, to provide the function of the Lung Enhancer accordingly, as herein specified, for a more accurate reading, through the above said conductive ability.

Another medical application, of the Lung Enhancer, utilizing existing technology as needed, but not limited to, is the ability to insert a data chip or any similar data retaining device or system, to provide information on the usage being performed by the patient. This unit that will transmit or receive data, located in the Lung Enhancer, allowing the therapist or doctor to examine the stored information, whether wireless or by other means, at such time that is deemed necessary. This said data can be retrieved, by removing the data retained on a chip, but not limited to, within the housing of the Lung Enhancer and by inserting a chip or similar unit that applies to data storage, into a PC board, (Computer), that is programmed to provide patient data that is being retrieved at that time.

An alternative answer to retrieving patient data usage, from the Lung Enhancer would be via, infra red, radio waves or similar systems, without the use of any data chips or systems, which will allow transmittal or receiving of data accordingly, from the medical apparatus which will provide the same aforementioned function and shall directly be sent to the PC, or any similar devices such as a hand held unit, similar to a palm pilot, for example an IR 1 FAIRCHILD QED233-ND Transmitter/Receiver, but not limited to these particular components, in order to retrieve or transmit data, from whatever location which is in appropriate range, in order to receive the aforementioned transmitted retrievable signal, that the doctor or therapist is located at any given time. This non-attached unit, would give the therapist or doctor the ability to retain and retrieve the particular patient's data as needed and have a complete breakdown of information of the amount of sessions, measurements, and information on stored data, necessary to properly treat the patient from another location, as deemed by the doctor or therapist, at any time desired.

A code, but not limited to, or similar way of specifying the particular patient, in which data is being retrieved, could simply be entered into the CP, or similar unit, but not limited to, allowing the doctor or therapist to designate which patient he or she is desiring medical information on at that time. This will reduce the valuable time spent, reading charts, or writing information for the doctor to view at a later time. The PC, or similar unit as described as herein, but not limited to, can be at any location deemed accordingly, making the retrieval of data simple and easily obtained. Through the use of the Lung Enhancer, not only will the Medical Industry benefit with this new improved incentive spirometry device, supplying an audible, verbal simulated human voice, which will inform the patient, that it is time for their therapy, what is their progress or volumes reached, when to try again or when to stop, but also the patient as well, for it is well known in the medical industry, "the more one uses the prescribed treatment, the faster one recuperates".

With the conception of the Lung Enhancer, a new step in medical progress will be made through a cost effective electronically enhanced new device, that guides the patient, under the SMI therapy as aforementioned, from start to finish, as well as prompts, nags, goes into "sleep mode," and wakes up to encourage usage. The use of an audible apparatus that gives information, or the ability to retrieve stored information data, is invaluable and will allow the patient to recover quicker, as well as, save money by providing a way to prescribe the proper treatment to those patients more effectively and comprehensively. Thus, by using the Lung Enhancer, quicker patient recovery will be achieved, through compliance, with less complications. Through the utilization of the present invention employing audible, verbal incentive, prompting the usage by the patient, through encouraging words and phrases, produced by the medical apparatus itself will not only benefit the sighted, but the blind as well, providing a more useful method to assure adequate recovery.

Through the improvement of using electronically simulated, audible, verbal, human sounding word, words, or phrases that emanate from within the Incentive Spirometer itself, the ability of this programmed new invention, has the intelligence to detect the patient's measurements, as well as prompting the exact time, that the patient should begin therapy again accordingly. This new improved apparatus, will also give the measurement of the volume that the patient has performed during their therapy, along with encouraging phrases that continue to lead and guide the patient until the full therapy is completed.

DETAILED DESCRIPTION OF THE INVENTION

Figure 1:
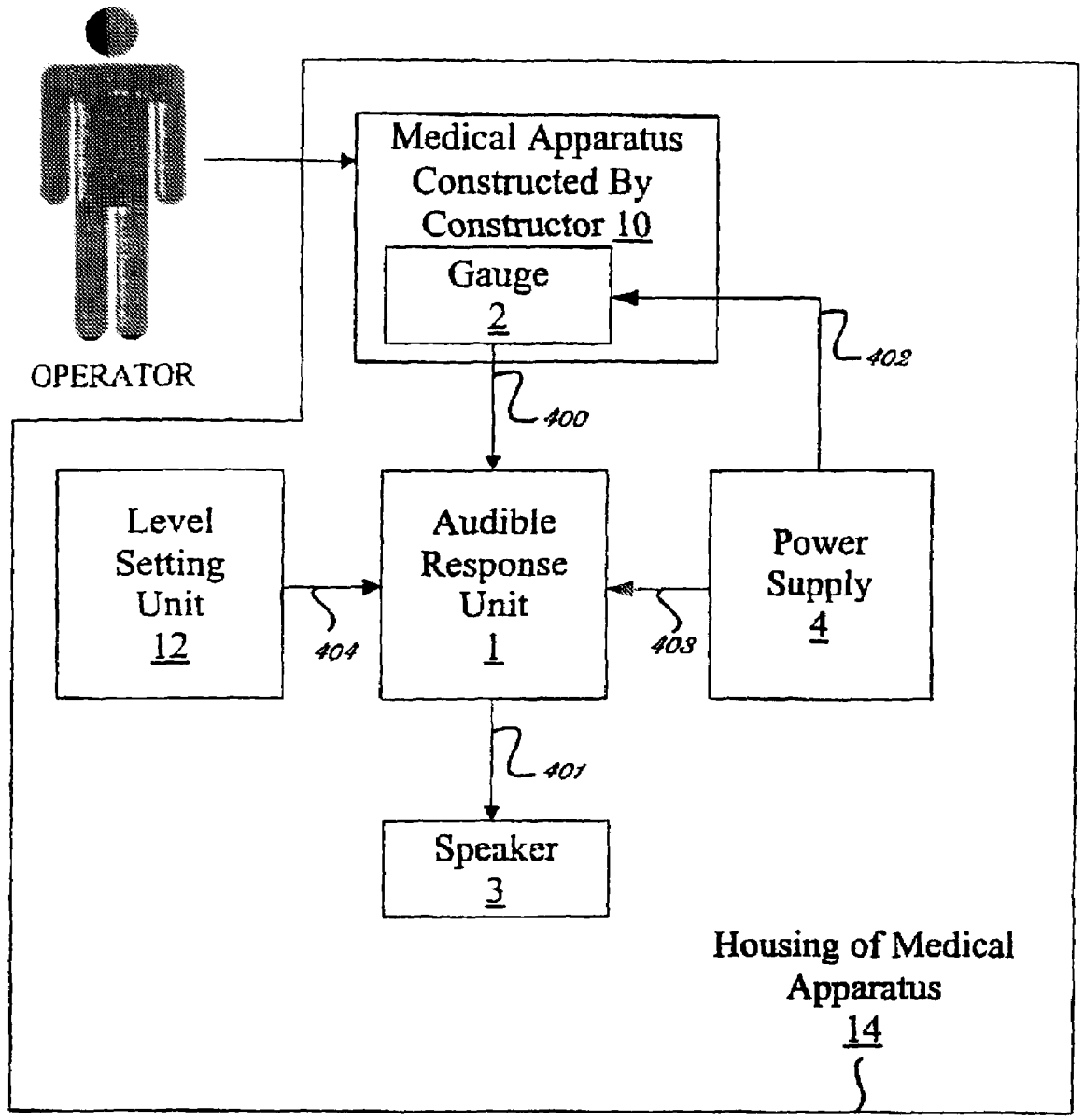
FIG. 1 shows a Preferred Embodiment of the Present Invention.

Now referring to the drawings the present invention will be further described. FIG. 1 shows a preferred embodiment of present invention. A Gauge 2 connects to Audible Response Unit 1 through one or more electrical connections labeled 400. Audible Response Unit 1 connects to Speaker 3 through an electrical connection labeled 401. Power is supplied from Power Supply 4 to Gauge 2 through an electrical connection labeled 402. Power is supplied from Power Supply 4 to Audible Response Unit 1 through an electrical connection labeled 403.

Figure 2:
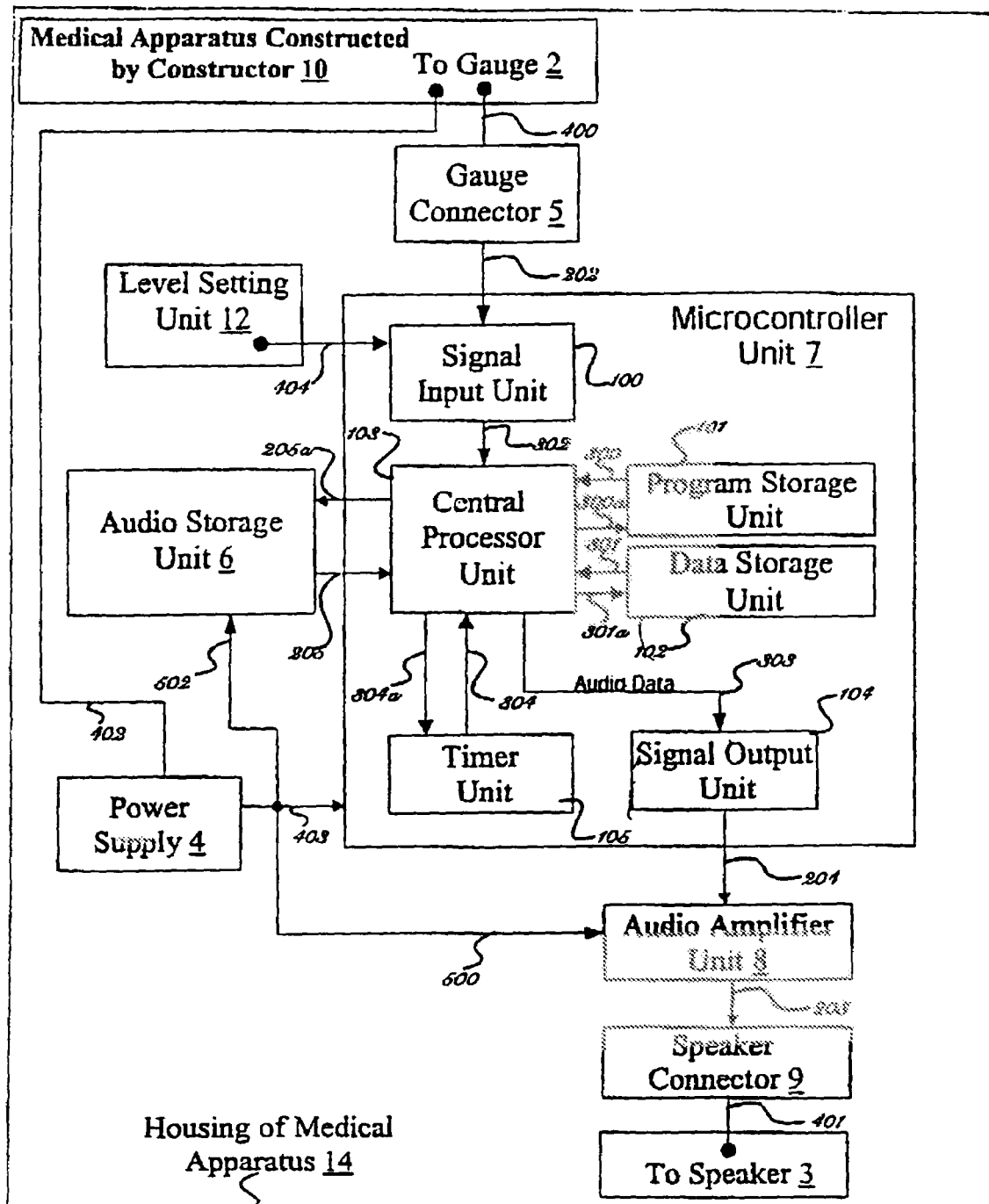
FIG. 2 shows the Preferred Embodiment of the Audible Response Unit.

FIG. 2 Shows the Preferred Embodiment of Audible Response Unit 1. Gauge 2 of FIG. 1 connects to Gauge Connector 5 through one or more electrical connections labeled 400. Gauge Connector 5 connects to Signal Input Unit 100 which is a subunit of the Microcontroller Unit 7 through one or more electrical connections labeled 202. Microcontroller Unit 7 contains subunits Signal Input Unit 100, Program Storage Unit 101, Data Storage Unit 102, Central Processor Unit 103, Signal Output Unit 104 and Timer Unit 105. Signal Input Unit 100 provides information to Central Processor Unit 103 through a set of signals labeled 302.

Central Processor Unit 103 receives a set of program instructions that provide the function of the Audible Response Unit 1 from Program Storage Unit 101 by providing control information through signals labeled 300a and receiving instructions through signals labeled 300. Information used by the program instructions are kept in Data Storage Unit 102 by providing control information and data to be stored through a set of signals labeled 301a and by receiving data through a set of signals labeled 301. Central Processor Unit 103 controls a set of timers in Timer Unit 105 through a set of signals labeled 304a and receives information from the timers in Timer Unit 105 through a set of signals labeled 304. The Central Processor Unit 103 uses information from Timer Unit 105 to determine accurate time intervals. Central Processor Unit 103 receives audio data from Audio Storage Unit 6 by providing control information through a set of signals labeled 205a and by receiving audio data through a set of signals labeled 205. Central Processor Unit 103 relays the audio data received from Audio Storage Unit 6 to Signal Output Unit 104 by transferring the audio data through a set of signals labeled 303. Signal Output Unit 104 transfers audio data to Audio Amplifier Unit 8 through a set of signals labeled 204.

Audio Amplifier Unit 8 transfers amplified audio data to Speaker Connector 9 through a set of signals labeled 203. Speaker Connector 9 connects to Speaker 3 of FIG. 2 through a set of signals labeled 401.

Figure 4:
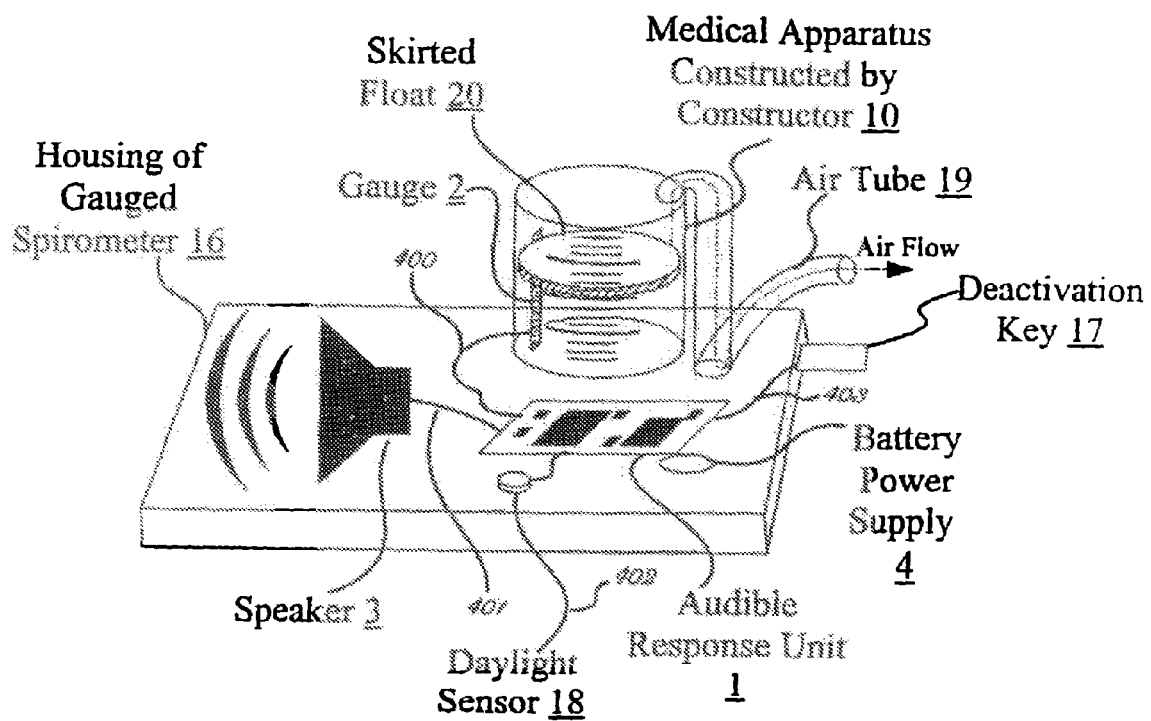
FIG. 4 shows the Present invention within the housing of a Medical Apparatus.

FIG. 4 shows the present invention within the housing of a Medical Apparatus 10, that implements a Gauged Spirometer whose housing is identified as 16 and which encloses the Medical Apparatus 10, which is comprised of the Speaker 3, Audible Response Unit 1, Battery Power Supply 4, Daylight Sensor 18, and Deactivation Key. Daylight Sensor 18 is used by the Audible Response Unit 1, that detects that it is nighttime by measuring the signal on 402 and comparing it to a value within the Data Storage Unit 102. Deactivation Key 17, deactivates the Audible Response Unit 1, that closes a switch that relays a signal over electric conductor 403, comparing it to a value within the Data Storage Unit 102, it enters an operational mode called "silent mode".

Figure 3:
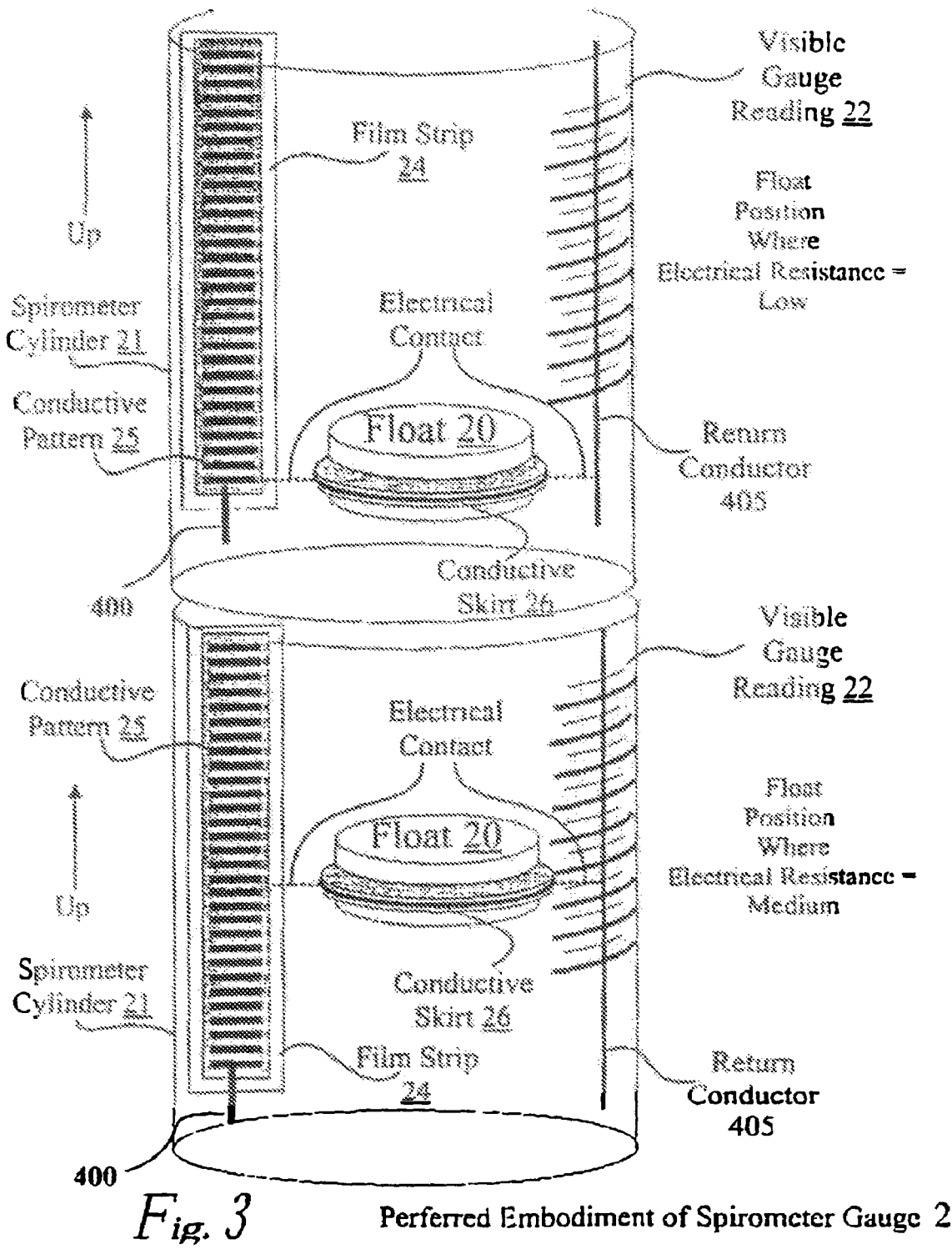
FIG. 3 shows the details of the Gauge.

FIG. 3 shows details of Gauge 2, where a Film Strip 24 is attached to the inside wall of the Incentive Spirometer Cylinder 21, covered with a Conductive Pattern 25. Float 20, which is covered with Conductive Skirt 26, moves freely up and down within the Incentive Spirometer Cylinder 21, making contact with Conductive Pattern 25 of Film Strip 24, to create an electric path from contact with Film Strip 24 and the Return Conductor 405. Current from electric conductor 400, through Film Strip 21, through Conductive Pattern 25, through Float Skirt 26, through Return Conductor 405, is proportional to the position of electrical contact, called "float signal". "Float Signal" is relayed to Audible Response Unit 1, by electric conductor 400, interpreted in Audible Response Unit 1 and is able to measure and record performance.

Figure 5:
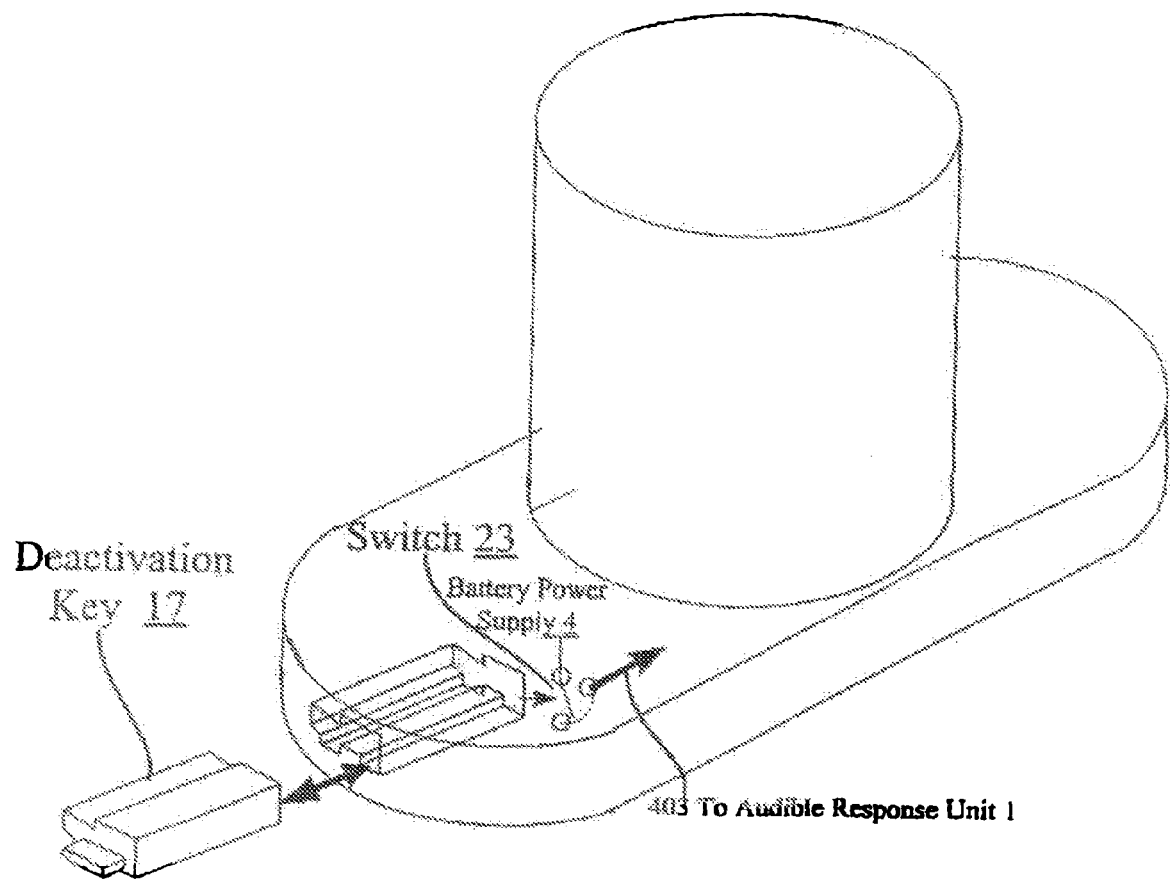
FIG. 5 shows the details of the Deactivation Key 17.

FIG. 5 Detail of Deactivation Key 17, which causes switch 23 to close, thus connecting Battery Power Supply 4, to electrical conductor 403, causing a signal on electric conductor 403, relayed to Audible Response Unit 1, interpreting the signal on electrical conductor 403.

When apparatus 10 in FIG. 1 is used by the operator, a gauge 2 within the apparatus produces an electrical signal on electrical conductor 400 proportional to the physical parameter that is measured by the gauge 2. The electrical signal on 400 is variable over time and represents an electrical representation of the parameter measured by the Gauge 2 during the duration of time that the Apparatus 10 is used. The electrical signal on 400 is input to the Audible Response Unit 1 where the electrical signal on 400 is evaluated.

The Gauge Connector 5 on FIG. 2 relays the electrical signal on 400 to the Signal Input Unit 100 within Microcontroller Unit 7 where the electrical signal on 400 is converted repeatedly at a fixed rate of once every unit of time called the "sampling interval" for the duration of time when the electrical signal on 400 is being evaluated. The Signal Input Unit 100 converts the electrical signal on 400 into a digital numerical format and relays it through a set of digital electrical signals 302 to the Central Processor Unit 302. This process is repeated after the transpiring of time equal to the sampling interval for the duration of time over which the electrical signal on 400 is being evaluated.

The parameter being measured by Gauge 2 is thereby converted to a sequence of numerical digital values that represent the magnitude of the parameter over the time duration when the parameter is being evaluated, and each successive numerical digital value represents the magnitude of the parameter measured by Gauge 2 at the time that is one "sampling time" interval later than the preceding numerical digital value.

The Central Processor Unit 103 executes a sequence of instructions that are retrieved from the Program Storage Unit 101. This sequence of instructions is called the "functional program" and defines the series of steps and decisions that are made to constitute the function of the present invention. The Central Processor Unit 103 retrieves the instructions from the Program Storage Unit 101 by presenting an index called a "program address" to the Program Storage Unit 101 through the set of digital electrical signals 300a. The "program address" is calculated by the Central Processor Unit 103 as directed by the instructions of the "functional program" that it is executing. The Program Storage Unit 101 responds to the "program address" on 300a by retrieving and relaying the instruction corresponding to the "program address" to the Central Processor Unit 103.

The instructions representing the "functional program" relayed to the Central Processor Unit 103 by the Program Storage Unit 101 over digital electrical signals 300a are executed by the hardware within the Central Processor Unit 103 to perform mathematical calculations, "program address" generation, and decision logic which together constitute the "functional program" of the present invention which in turn defines the behavior and function as defined for the Apparatus 10.

Intermediate mathematical and logical calculations that are preformed by the Central Processor Unit 103 as it executes the "functional program" result in information collectively called "data" that are stored in the Data Storage Unit 102. The Central Processor Unit 103 identifies storage locations in the Data Storage Unit 102 for storing or retrieving "data" by presenting an index called the "data address" to the Data Storage Unit 102 through a set of digital electrical signals 301a. The Central Processor Unit 103 generates the "data address" by performing calculations that it is directed to perform by the instruction of the "functional program" that is being executed. The Central Processor Unit 103 also presents "data" to be stored through the set of digital electrical signals 301a to the Data Storage Unit 102. If the Central Processor Unit is retrieving data from the Data Storage Unit 102, the Data Storage Unit 102 presents the retrieved data associated with the "data address" on 301a to the Central Processor Unit 103 through a set of digital electrical signals 301.

The Central Processor Unit 103 directs the Timer Unit 105 by presenting commands that are calculated during the execution of the "functional program" to the Timer Unit 105 through a set of digital electrical signals 304a. The commands instruction Timer Unit 105 on the time intervals that are to be generated. The Timer Unit 105 relays time interval information to the Central Processor Unit 103 through a set of digital electrical signals 304. The Central Processor Unit 103 uses the timer interval information for purposes of indicating when one or a set of instructions of the "functional program" should execute. The Central Processor Unit 103 has the ability to synchronize the execution of one or a set of instructions of the "functional program" to a precise point in time or an interval of time.

When the Central Processor Unit 103 determines that an audible response is needed and which audible response is to be generated as determined by the definition of the behavior of the Apparatus 10 and the definition of the "functional program", it is directed by the instructions within the "functional program" to calculate an index called the "audio address" that is used to retrieve the audible response data called "audio data" from the Audio Storage Unit 6. The Central Processor Unit 103 presents the "audio address" to the Audio Storage Unit 6 through a set of digital electrical signals 205a. The Audio Storage Unit 6 responds by relaying the "audio data" associated with the "audio address" to the Central Processor Unit 103 through a set of digital electrical signals 205.

The Central Processor Unit 103 retrieves time interval information from Timer Unit 105 to determine the appropriate time when retrieved "audio data" can be relayed to the Signal Output Unit 104. In this way, the "audio data" is successively relayed to the Signal Output Unit at a rate appropriate for the regeneration of the audible response from the "audio data". The Central Processor Unit 103 relays the "audio data" to the Signal Output Unit 104 through a set of digital electrical signals 303.

The Signal Output Unit 104 receives "audio data" from the Central Processor Unit 103 at a rate that is indicated by time interval from the Timer Unit 105. The time interval is calculated by the Timer Unit 105 as it is commanded to do by the Central Processor Unit 103 when it executes the instructions in the "functional program" that controls setting up of the Timer Unit 105. The time interval is made to be the value required in order to regenerate the audible response correctly when "audio data" is repetitively output at a rate equal to the time interval.

The Signal Output Unit 104 receives "audio data" in a digital numerical form from the Central Processor Unit 103 repetitively starting from the first unit of "audio data" to the last unit of "audio data". The Signal Output Unit 104 converts the "audio data" to an electrical signal whose magnitude is proportional to the "audio data" repetitively for each "audio data" received. It relays the electrical signal to the Audio Amplifier Unit 8 through an electrical signal 204. The Audio Amplifier Unit 8 multiplies the magnitude of the electrical signal relayed on the electrical signal 204 such that the amount of power represented by the electrical signal 204 is increased and output to the Speaker Connector 203. The Speaker Connector 9 relays the amplified electrical signal on 203 to electrical signal 401 which corresponds to electrical signal 401 on FIG. 2. The amplified electrical signal 401 is presented to the Speaker 3 in FIG. 2.

The Speaker 3 converts the amplified electrical signal 401 to sound energy that represents the audible response that the Audible Response Unit 1 has calculated in response to the measurement of a parameter that is determined by the Gauge 2 of the Apparatus 10 in accordance to the defined behavior of the Apparatus 10 and of the defined function of the "functional program."

The present invention describes a method of producing audible response to the measurement of a parameter by an Apparatus 10 so that the audible response is done according to a defined behavior determined by the constructor of the Apparatus 10. Implementation of the defined behavior of the audible response to measurement of a parameter within the Apparatus 10 is realized by the defined function of the "functional program" that is coupled to the Audible Response Unit 1 by storing the "functional program" in the Program Storage Unit 101 within the Audible Response Unit 1 and by providing a means for the Central Processor Unit 103 within the Audible Unit 1 to execute the instructions in the "functional program" and to perform the actions as they direct the Central Processor Unit 103 and the other subunits within the Audible Response Unit 1.

FIG. 4 shows the Present Invention within the housing of a Medical Apparatus 10 that implements a Gauged Incentive Spirometer whose housing is identified as 16 and which encloses the Medical Apparatus 10 as well as the present invention which is comprised of the Speaker 3, Audible Response Unit 1, Battery Power Supply 4, Daylight Sensor 18, Deactivation Key 17. The Medical Apparatus in this embodiment is constructed to perform Incentive Spirometry measurements of the medical patient referred herein as the "operator". In this embodiment of the present invention, the Power Supply 4 is implemented as a Battery in order to provide a means of operating the Medical Apparatus without the need to connect to an auxiliary power source through means of wire cords. This means is referred to as using a "cordless" power supply.

The present invention also includes a Daylight Sensor 18 that is used by the Audible Response Unit 1 to distinguish between daylight and nighttime. The Daylight Sensor 18 is constructed as but not limited to a photocell that relays a signal to the Audible Response Unit 1 over electrical conductor 402. When the Audible Response Unit 1 detects that it is nighttime by measuring the signal on 402 and comparing it to a value within the Data Storage Unit 102, it enters an operational mode called "silent mode". In "silent mode", the Audible Response Unit 1 activates itself at the same time intervals as it does in daytime, but does so in order to measure the daylight by means of sensing the Daylight Sensor 18. If sufficient daylight is not detected, the Audible Response Unit 1 does not emit any audible instructions to the operator but instead sets an internal timer to reactivate itself after a prescribed time interval that is defined in the "functional program" of the Audible Response Unit 1 and then deactivates itself. With this method of daytime detection, it is possible for the Audible Response Unit 1 to permit the "operator" to rest during the nighttime and to maintain a regular programmed interval for reactivation. When the Audible Response Unit 1 is reactivated at the transpiring of the programmed time interval as defined in its "functional program" and detects sufficient daylight, the Audible Response Unit 1 enters an operational mode called "standard mode" and begins emitting audible commands to the "operator" as defined by the "functional program" within the Audible Response Unit 1.

The present invention also includes a Deactivation Key 17 that provides to the means to deactivate the Audible Response Unit 1 for any period of time in the event that such deactivation is determined to be necessary by qualified personnel responsible for the medical care of the "operator". The Deactivation Key 17 is a mechanically unique shape that matches the same mechanically unique cavity within the Housing of the Gauged Spirometer 16. The Deactivation Key 17 when inserted into the housing of the Gauged Spirometer 16 closes a switch that relays a signal over electrical conductor 403 to the Audible Response Unit 1 to indicate the presence of the Deactivation Key 17. When the Audible Response Unit 1 detects that the Deactivation Key 17 is present by measuring the signal on 403 and comparing it to a value within the Data Storage Unit 102, it enters an operational mode called "silent mode". In "silent mode", the Audible Response Unit 1 activates itself at the same time intervals as it does in "standard mode", but does so in order to measure the presence of the Deactivation Key 17 by sensing the signal on 403. If the Deactivation Key 17 is determined to be present, the Audible Response Unit 1 does not emit any audible instructions to the operator but instead sets an interval timer to reactivate itself after a prescribed time interval that is defined in the "functional program" of the Audible Response Unit 1 and then deactivates itself. With this method of detection of Deactivation Key 17, it is possible for the Audible Response Unit 1 to permit the qualified personnel to deactivate the Audible Response Unit 1 for any period of time and to maintain a regular programmed interval for reactivation. When the Audible Response Unit 1 is reactivated at the transpiring of the programmed time interval as defined in its "functional program" and detects the absence of the Deactivation Key 17, the Audible Response Unit 1 enters an operational mode called "standard mode" and begins emitting audible commands to the "operator" as defined by the "functional program" within the Audible Response Unit 1.

FIG. 3 shows details of Gauge 2 as constructed for the Incentive Spirometry application shown in FIG. 4. The Gauge 2 is constructed of a thin Film Strip 24 of resistive material typically consisting of but not limited to carbon or graphite. The Film Strip 24 is attached to the inside wall of the Incentive Spirometer Cylinder 21 with adhesive. The surface of the Film Strip 24 that faces the interior of the Spirometer Cylinder 21 is covered with a Conductive Pattern 25. The Float 20 is free to move up and down within the Incentive Spirometer Cylinder 21 and makes contact with the interior facing surface's Conductive Pattern 25 of Film Strip 24 at a point that corresponds to the height position of the Float 20. The outer edge of the Float 20 that contacts the interior facing surface of the Film Strip 24 is covered with a Conductive Skirt 26. The Conductive Skirt 26 creates an electrical path from the position of contact with the Film Strip 24 and the Return Conductor 405. The Float 20 rises as the "operator" inhales through the Air Tube 19 of FIG. 6 so that the gas pressure above the float is lower than the gas pressure beneath the float which is at standard 1 atmosphere. The Float 20 ceases rising when the difference between the gas pressure above and beneath the Float 20 multiplied by the cross sectional surface area (in the direction of the axis of the Spirometer Cylinder 21) of the Float 20 is equal than the weight of the Float 20. The Float 20 falls when the difference between the gas pressure above and beneath the Float 20 multiplied by the cross sectional surface area (in the direction of the axis of the Spirometer Cylinder 21) of the Float 20 is less than the weight of the Float 20.

The amount of electrical current flowing from the electrical conductor 400 through the Film Strip 21 through Conductive Pattern 25 through the Float Skirt 26 through the Return Conductor 405 referred to as the "float signal" is proportional to the position of the electrical contact between the Conductive Pattern 25 and the Float Skirt 26 referred to as the "contact point". The higher the "contact point" is, the more distance there is between the electrical conductor 400 and the "contact point" and hence the more resistive material that comprises the Film Strip 21 there is, and the higher the electrical resistance there is to current flow from electrical conductor 400 to the Return Conductor 405. The position of the contact point corresponds to the height position of the Float 20. Therefore, the amount of electrical current of the "float signal" through electrical conductor 400 is proportional to the height position of the Float 20. The higher the position of the Float 20, the less electrical current there is flowing through the electrical conductor 400 at the "float signal". The lower the position of the Float 20, the higher the electrical current there is flowing through the electrical conductor 400 at the "float signal".

The "float signal" is relayed to the Audible Response Unit 1 by electrical conductor 400 and is interpreted by the "functional program" in the Audible Response Unit 1. The Audible Response Unit 1 takes measurements of the "float signal" and determines the level of the signal that corresponds to when the Float 20 reaches it's apogee and when it settles back down to the bottom of the Spirometer Cylinder. By making this determination, the Audible Response Unit is able to measure and record the performance of the "operator" as measured by the Incentive Spirometer.

FIG. 5 shows a detail of an example of embodiment of the Deactivation Key 17. It is comprised of a uniquely mechanically shaped device that fits precisely into a cavity within the Housing of the Gauged Incentive Spirometer 16. When successfully inserted into this cavity, the Deactivation Key 17 causes switch 23 to close thereby connecting the Battery Power Supply 4 to the electrical conductor 403. The connection of the Battery Power Supply 4 through switch 23 causes a signal on electrical conductor 403 that is relayed to the Audible Response Unit 1. Audible Response Unit 1 interprets the signal on 403 as described in the previous description of FIG. 3 Some of the advantages and features of my invention include:

I. Electronic technology which has been especially developed to work within the incentive spirometer, that will help the patient by providing simulated audible, verbal, human sounding voices, thus providing instructions, prompting appropriate usage according to therapeutic time schedules, correcting and encouraging patient performance, as well as, giving the appropriate measurement, that the person or patient has performed with the apparatus, eliminating human visual error, help assist the blind and the visually impaired, through the use of today's state of the art equipment, that can produce electronic intelligence within the apparatus at a low cost, thus reducing patients recovery time and complications, 1) a method of providing audibly and verbally, instruction and guidance, to help perform the therapeutic sessions by the patient to improve lung performance, which through medical studies has shown that very few patients perform the required therapy as suggested through the accompanied literature, but through the usage of the present invention, the percentage in regards to lung problems occurring due to failure of patient usage of the Incentive Spirometer, will decease dramatically as the present invention will nag or prompt the patient without stopping, until the patient uses the apparatus and will not stop until the time interval necessary to fulfill the patient's therapeutic need has been accomplished. Through electronic intelligence, the present invention, will prompt the patient to use the medical apparatus, as well as, guide the patient through the proper steps of using said medical apparatus, thus quicker patient recovery will be achieved, through compliance without complication, 2) replacing the normal human visual readings or measurements, eliminating human error of inaccurate readings, due to the prior required float recognition which is imperative to provide visual measurement, since the float doesn't stay always in position long enough to read properly and has to be constantly viewed during therapeutic sessions to observe the exact reading of measurement, with a human sounding electronically programmed voice or voices giving the same readings or measurements as deemed necessary to provide the sighted, as well as the visually impaired patient, with adequate information, to fulfill the patient's therapeutic regiment for recovery and allowing the blind to hear and respond, to the full operation of the therapeutic regiment, of the present invention;

3) a medical apparatus that because of the inexpensive construction, is comparable to the same concept, in relationship to therapeutic use, as the expensive apparatus, due to today's advanced technology. This breakthrough in modern technology allows the patient to afford the new improved apparatus of the present invention, which basically supplies all of the same healthcare purposes in relationship to the therapy of the apparatus, however, it also gives the patient the advantage of hearing the therapeutic guidance and measurements as an added benefit and cost is virtually the same as most disposable incentive spirometry units;

II. A new method to provide the above function of the present invention through the following electronic technology:

1) a number of the following electronic components in order to provide the function as above mentioned:

(a) one or more electronic sensors producing an output signal, (b) one or more electronic modules that convert said sensor output signal (s) into digital format, (c) one or more electronic modules that includes but is not limited to a central processing unit, (d) one or more electronic modules for digital storage of program instructions and data, (e) one or more electronic modules for digital storage of digital audio sound data, (f) one or more electronic modules for generation of audible sound, (g) one or more electronic modules for managing and conserving electrical power, (h) one or more electronic modules for determining accurate intervals of time, (i) one or more electronic modules for communicating remotely with separate agent, (j) one or more electronic sensor for detecting light or the absence of light to turn off or on unit 2) said method of new apparatus capable of measuring output signal of the sensors, converting said output signals into digital format to be stored and processed by the central processing unit, resulting in actions taken by the central processing unit under direction of it's digital program instructions in accordance to it's pre-determined set of actions, 3) said pre-determined actions of the digital program instructions include but not limited to the generation of audible audio sound sequences that provide information relating to said output signals, 4) said electronic sensors capable of measuring but not limited to parameters of performance of the human body in various settings relating to medical therapeutic performance, or physical training, 4a) said electronic sensors being comprised of, but not limited to, a resistor that forms a variable resistance to electric current flow, such as a film of carbon, but not limited to, that forms a resistance to electric current flow, in contact with said resistor, 5) said central processing unit capable of performing tasks as specified in the order defined in digital program, including, but not limited to processing of sensor output signals, execution of control functions defined by the digital program, providing actions in accordance to accurate time intervals, generation of audible sound, 6) said digital program defines control functions that implement therapy or physical rehabilitation regimes, 7) said digital program defining control functions that implement tasks for managing and conserving electrical power, 8) said digital program defining control functions that implement tasks for determining accurate intervals of time, 9) said digital program defining control functions that implement tasks for determining time of day, (for those medical apparatus that need to be turned on or off to begin or end therapeutic sessions), 10) said digital program defining control functions that implement tasks for communicating with a separate agent, 11) said digital program being stored in memory within the electronic module that contains the central processing unit, and or being stored in memory that is not within the electronic module that contains the central processing unit but that is accessible by the central processing unit, 12) said digital audio sound data being stored in memory within the electronic module that contains the central processing unit, and or being stored in memory that is not within the electronic module that contains the central processing unit but that is accessible by the central processing unit, 13) directory table containing descriptive information about those commands, responses, measurements, or words as aforementioned about said digital audio sound data that is stored in memory within the electronic module that contains the central processing unit, or being stored in memory that is not within the same electronic module that contains the central processing unit but that is accessible by the central processing unit, 13a) said digital audio sound data being arranged into multiple units, each unit representing an audible verbal message comprised of a series of words as programmed per the requirements in synthesis with the medical apparatus's therapeutic use, 13b) a method for retrieving and generating the audible sound representing the digital audio data from the start of the message to the end of the message as corresponds to the therapeutic dialogue needed, 13c) a method for retrieving and generating the audible sound representing the digital audio data from an intermediate pint in the message to a subsequent intermediate point in the same message, to allow the medical apparatus to respond to the measurements being produced by the patient accordingly and guide the patient according to the measurement amount, 14) said electronic module for generation of audible sound being the same electronic module that contains the central processing unit, and or a being separate electronic module for the module that contains the processing unit, 15) said electronic module for generation of audible sound including a module that converts digital audio data into continuous analog signal that is amplified to increase the signal power as needed to create audible sound from sound generating modules such as, but not limited to, speakers, 15a) Said electronic modules for generation of audible sound providing a sound generating a continuous analog signal that is one half the value of the maximum signal level, such level representing zero sound to be generated, 15b) said electronic module for generation of audible sound providing a sound generating module such, but not limited to, speaker(s) that is capable of receiving a level that is one half the maximum signal level in a way that produces no sound and consumes little or no power, 15c) said sound generating module such as, but not limited to, a speaker(s) whose reference signal level is set at one half the maximum signal level such that it produces no sound when it receives such a signal level, 15d) said sound generating module being provided a reference signal level set at on half the maximum signal level by connecting it between a series of batteries in a way that provides a reference signal that is exactly on half the signal level that is produced by the above said batteries connected in this way, 16) said digital program defining a method for determining the value of a sensor output signal, generating an audible verbal response according to a pre-determined set of controls and functions as described herein, in order to provide instructional information to the operator of whatever medical apparatus is being used for instructional information or guidance, 17) said digital program defining a set of pre-determined set of controls and functions relating sensor output signals to audible verbal commands, responses and measurements, comprises of improving medical conditions of the patient through the use of the said medical apparatus accordingly, along with the present invention.

Furthermore the present invention can include a deactivation chip, which is different from slip chip that can also be used with the present invention. The slip chip can be a component of the invention that can be removed to start the Incentive Spirometer when the nurse or other person removes the slip chip from the unit. The slip chip can also be replaced back to stop the unit from automatically sending voice messages (as programmed for the patient) should there be a need that requires the apparatus or unit to be turn off.

The deactivation chip can be comprised of basic components, such as, but not limited to, the microcontroller, chip (semiconductor) and circuit boards and can be configured or assembled as one removable unit. These components can be reused (even with a disposable Incentive Spirometer) by removing the unit consisting of the components prior to disposing with the rest of the Incentive Spirometer. This, feature helps to save cost for a hospital, patient, etc., as these components can be reused with another Incentive Spirometer for another patient. Thus, when the patient has completed the therapeutic sessions and does not need the Incentive Spirometer, the unit consisting of the components can be removed and used again in the next Incentive Spirometer that is brought in. Several deactivation chips can also be used as needed for more than one patient. The removable unit can be referred to as a deactivation chip since when the unit is removed the components of the unit turn off (i.e. deactivate). The removable unit can be preferably incapsulized so that it is noncontaminated from the patient using the Incentive Spirometer, which thus allows the unit to be removed and reused.

Figure 6:
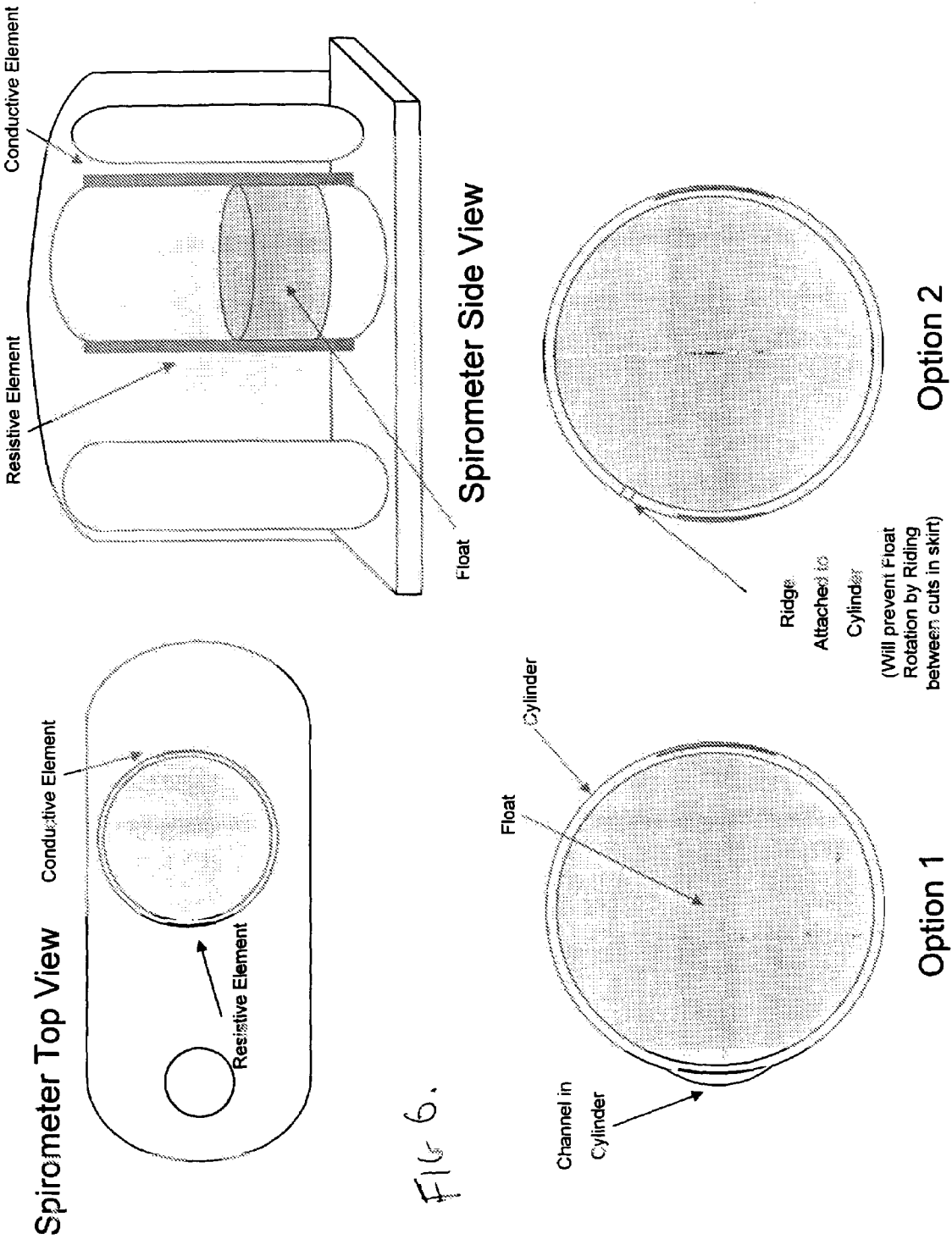
FIG. 6 illustrates several views of one Incentive Spirometer embodiment for the present invention showing the Incentive Spirometer having a float stop member.

FIG. 6 illustrates stop member for the Incentive Spirometer which prevents the float from significantly moving within the cylinder (housing) in the horizontal plane such that the conductive area of the skirt remains properly aligned with the conductive area (i.e. conductive strip on cylinder wall) on the cylinder for making appropriate contact needed for accurate measurement readings. The measurement readings can then be sent through an output signal to the proper components for further processing. In one embodiment the stop member can be a guiding rod or protrusion or an indention in the molding of the housing itself that could run the extent of the cylinder containing the float (with a means within or on the float that would follow the guide, in order to keep the float aligned). In another embodiment a ridge or protrusion can stick out enough within the cylinder and fit within an indention or cutout on the float itself.

Figure 7:
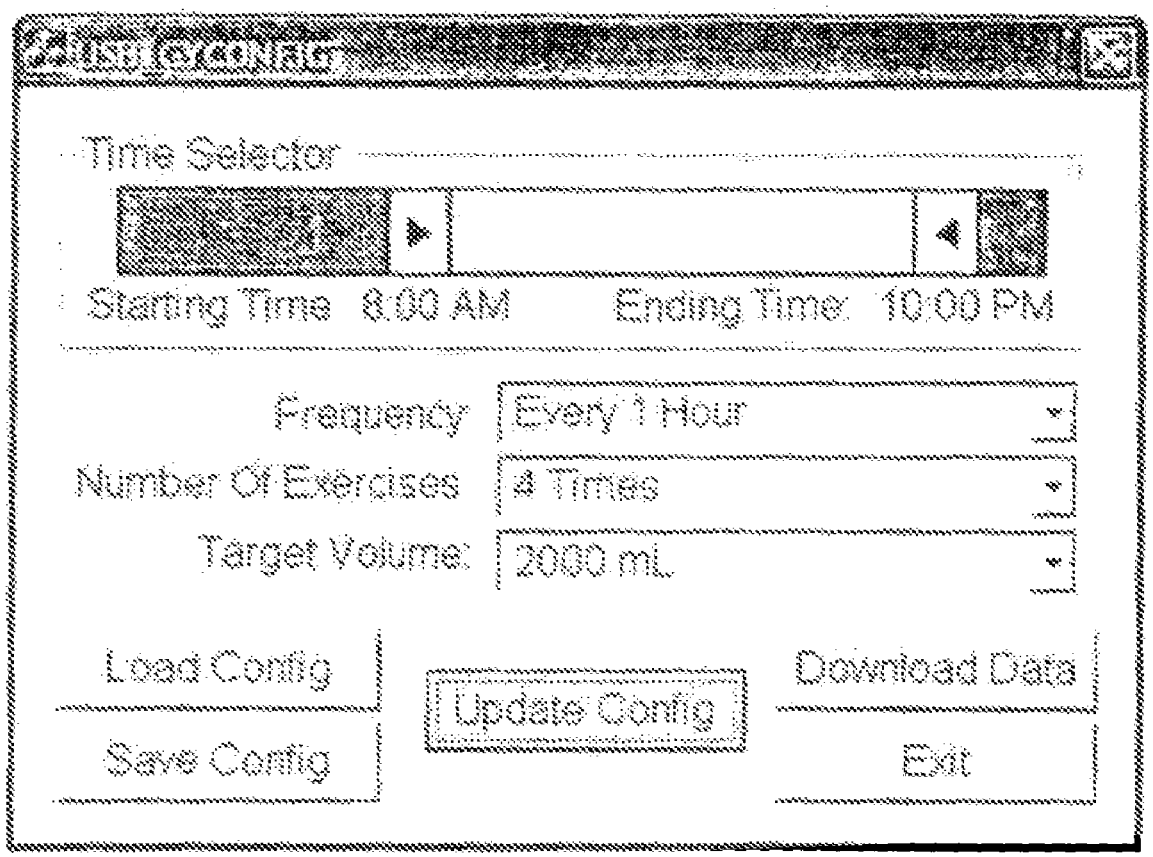
FIG. 7 illustrates a screen shot for the PC software interface for communicating with the Incentive Spirometer of the present invention.

FIG. 7 illustrates a screen shot for one configuration or embodiment of a PC or computer software interface for a base station. The base station provides an alternative mechanism for customizing the Incentive Spirometer by allowing the doctor or whoever to set the time between sessions, turn off times (i.e. without using a photosensor), etc. However, it should be recognized that the Incentive Spirometer can be programmed or customized without the use of a base station and the present invention does not require a base station to fulfill the functions as described above. The base station provides an optional mechanism for the user. The base station also has the ability to allow the operator or person programming or retrieving data to place the Incentive Spirometer in a molded like area for both customizing and retrieving the data stored within the Incentive Spirometer regarding the patient's performance(s) from using the Incentive Spirometer (i.e. measurement readings). The platform for the base station can be provided with one or more pins that insert in the bottom of the chip on the Incentive Spirometer to allow conductivity to perform these said functions. This feature allows the Incentive Spirometer, or any other medical device, to communicate with a computer for working with medical data, and any adjustments can be made on the screen, such as, but not limited to the adjustment capabilities shown on the screen of FIG. 7. Any adjustment(s) made can then be sent to the electronic components of the Incentive Spirometer through the base station. The Incentive Spirometer can be adjusted or transmit or its medical date through physical connection, such as, but not limited to, through a docking or base station or it can receive and/or transmit information (i.e. adjustment, medical date, etc.) through wireless technology.

The computer will be able, such as by using a curser controlled by a keyboard, mouse, and/or similar devices, (thus avoiding the need for a large apparatus), to make the programming of the Incentive Spirometer simple. In one embodiment, in addition to the computer, a means for holding the Incentive Spirometer (i.e. docking or base station, etc.) is provided to retain the Spirometer, while one uses their mouse and/or keyboard on the computer to adjust or customize the program stored on the Incentive Spirometer. Similarly, the user can also obtain any data stored by the Incentive Spirometer.

In one embodiment, the base station can form a mold in the shape of part of the Incentive Spirometer where the programming area is connected, such as, but not limited to the bottom of the Spirometer where the electronic components to facilitate the functions of the present invention can be preferably located. The actual shape is not considered limiting. It is preferred that there is some correspondence in shapes between the relevant portions of the spirometer and base station, so that the physical mating of the two components is accomplished easier. Alternatively, the base station can be sized and/or shaped to encompasses or accommodate more than one size of Spirometer or medical apparatus, and can be manually adjusted to fit or correspond to the size and shape of the apparatus that is connected thereto.

The base station can be a device which facilitates interface to a PC or computer via a USB cable for customization and data download of the Incentive Spirometer, back and forth wireless transmissions can also be communicated through or controlled by the base station. In one embodiment, the Incentive Spirometer can be pressed down onto the base station and the base station can be plugged into the PC or computer, such as through a cable, cord, USB port, etc. The screen shot illustrated in FIG. 7 shows one non-limiting version of the software interface on the PC or computer which can be used to communicate with the Incentive Spirometer. The following represents a summary of the functionality of the base station/PC(computer)/Software combination.

Time Selector: The upper bar on the screenshot can change the "Active Time" of the unit. Any session times outside of the window will not activate the Spirometer so that the patient can sleep or otherwise not be disturbed.

Frequency: Standard Frequency of testing can be every 1 Hour, though such is not considered limiting. This can be adjusted in 15 minute intervals or any other desired interval and all are considered within the scope of the invention.

Number of Exercises: The patient can be required to do several exercises (i.e. 4, etc.) exercises every session by default. The number of exercises per session can be adjusted.

Target Volume: This can be an optional parameter. The Hospital or other user can set this target volume to a value appropriate for each patient.

Load Configuration: This can be a convenience button. One can load up the configuration for "Standard Patient" or "Senior Male" or "Female Child". There may be some standard set of parameters that the hospital wants to use for different classes of patients.

Save Configuration: Where values to a group of settings that may be used commonly are set, one can save it off to a file for easy retrieval.

Update Configuration: Write the configuration data to the Serial FLASH.

Download Data: The Incentive Spirometer stores exercise result data in the Serial FLASH. This data can be downloaded and saved to a file on the PC or computer by using the Download Data button to confirm patient compliance.

Thus an interface for configuring the Spirometer via the base station can be provided. The top bar can provide times that the Spirometer is "Awake". i.e., it won't prompt the patient at any time outside of this time band so they can sleep. Thus, the Spirometer can be programmed, customized and adjusted, using the base station, according to the current therapeutic requirements of the patient. In summary, the base station provides a means for programming a particular apparatus (i.e. Incentive Spirometer, etc.). The base station can comprise a means through a connective source that combines measurements, instructions, specific target goals, predetermined values and intervals for rest periods, that may be needed between particular exercises, in order that those therapeutic guidelines are combined in synthesis with whatever apparatus is being programmed. This is not only limited to solely therapeutic needs, as a "timer" may be used for various medical requirements, such as, but not limited to, washing a valve, etc. The base station provides a means for programming the Incentive Spirometer with the therapeutic guidelines, per the particular requirements needed, for the patient and physician's specifications and provides a way for adjusting or customizing each Incentive Spirometer to the specific needs of the patient.

Thus, the Incentive Spirometer, with or without the base station, can be programmed or customized for any adjustments that relate to the exact therapeutic requirements desired by the one who is setting the Incentive Spirometer, within the guidelines of the apparatus, including, but not limited to, period of time in which the unit turns off as well as turns back on to allow for a sleep period for the patient.

It should be recognized the present invention is not considered limited to any specific type of Incentive Spirometer or Incentive Spirometry device. The present invention improvements can be incorporated into any and all Incentive Spirometry devices including, but not limited to, flowrate and volumetric, and all are considered within the scope of the invention. Furthermore, the present invention improved Incentive Spirometry devices can be provided in a disposable or non-disposable construction or configuration and both are considered within the scope of the invention.

It is also within the scope of the invention to use any means for providing flowrate measurements using said verbal employment, including, but not limited to millions of microelectronic hairlike components situated on the area of breathing, measuring the float within the cylinder of the apparatus by conductive strips or by infra red light placed beneath the float or similar unit for determining the volumetric measurements, but not limited to this particular exact means, etc. All capable measuring embodiments are considered within the scope of the invention for achieving the function of the device.

Though the preferred embodiment for the present invention does not use beeps or other audible noises for prompting, it is within the scope of the present invention to also use beeps or audible noises for prompting purposes. As the present invention uses audible messages, such as verbal voice messages, the benefits of the improved Incentive Spirometry devices of the present invention can also be experienced by a "blind" person, who is unable to see visual images.

Thus, in the preferred embodiment the present invention discloses an Incentive Spirometer that audibly, verbally prompts, encourages usage, commands, responds, and/or gives measurements, using humanlike voices to increase compliance by a person utilizing the Incentive Spirometer.

It will be seen that the objects set forth above, and those made apparent from the foregoing description, are efficiently attained and since certain changes may be made in the above construction without departing from the scope of the invention, it is intended that all matters contained in the foregoing description shall be interpreted as illustrative and not in a limiting sense. The instant invention has been shown and described herein in what is considered to be the most practical and preferred embodiment.

What is claimed is:

1. An Incentive Spirometer assembly and apparatus for programming, comprising:
    an Incentive Spirometer device,
    means for automatically prompting a user with a verbal voice message to use the Incentive Spirometer device to perform a sustained maximal inspiration (SMI) procedure;
    a docking station for programming said means for automatically prompting regarding use of said Incentive Spirometer device;
    wherein said means for automatically prompting is an electronic assembly in communication with a speaker and means for powering said electronic assembly, said electronic assembly comprising a microcontroller unit and an audio storage unit, said audio storage unit having at least one stored verbal voice message for prompting the user to use the Incentive Spirometer device to perform the sustained maximal inspiration (SMI) procedure; wherein said microcontroller unit directs the audio storage unit to automatically send a first verbal voice message to the speaker in order to prompt use of the Incentive Spirometer device by the user; and
    means for preventing said microcontroller unit from directing the audio storage unit to send the first verbal voice message, measurements or other verbal voice messages during certain conditions;
    wherein the certain conditions is level of darkness or light in a room in which the Incentive Spirometer device is located to provide the user with a sleep period without disturbance from said means for automatically prompting.

2. The Incentive Spirometer assembly of claim 1 wherein said means for preventing is a photosensor to detect the darkness or light in the room, said photosensor being in communication with the microcontroller unit.

3. An Incentive Spirometer assembly and apparatus for programming, comprising:
    an Incentive Spirometer device,
    means for automatically prompting a user with a verbal voice message to use the Incentive Spirometer device to perform a sustained maximal inspiration (SMI) procedure;
    a docking station for programming said means for automatically prompting regarding use of said Incentive Spirometer device;
    wherein said means for automatically prompting is an electronic assembly in communication with a speaker and means for powering said electronic assembly, said electronic assembly comprising a microcontroller unit and an audio storage unit, said audio storage unit having at least one stored verbal voice message for prompting the user to use the Incentive Spirometer device to perform the sustained maximal inspiration (SMI) procedure; wherein said microcontroller unit directs the audio storage unit to automatically send a first verbal voice message to the speaker in order to prompt use of the Incentive Spirometer device by the user; and
    means for preventing said microcontroller unit from directing the audio storage unit to send the first verbal voice message, measurements or other verbal voice messages during certain conditions;
    wherein said means for preventing is a deactivation key assembly in communication with the microcontroller unit which prevents the user from turning the means for automatically prompting on and off.

4. An Incentive Spirometer assembly and apparatus for retrieving data, comprising:
    an Incentive Spirometer device,
    means for verbally indicating and verbally responding accordingly to a user a measurement achieved by the user from the user's performance of a sustained maximal inspiration (SMI) procedure with the Incentive Spirometer device; and
    a docking station for retrieving data from said means for verbally indicating regarding a user's use of the Incentive Spirometer device
    wherein said means for verbally indicating comprising:
    an audio response unit;
    means for powering said audio response unit; and
    a speaker in communication with said audio response unit;
    wherein the signal is sent to the audio response unit which generates a verbal voice message which is sent to the speaker to verbally indicate to the user said volumetric or flowrate and Tidal volume measurement readings and also sends a verbal functional voice message appropriate for the measurement reading.

5. The Incentive Spirometer assembly of claim 4 wherein said audio response unit including an audio message storage unit which sends a verbal encouragement voice message to the speaker based on a comparison of the measurement reading to a target measurement, wherein said target measurement is a highest inhalation volumetric flowrate and Tidal volume previously performed by the user with the Incentive Spirometer device.

6. The Incentive Spirometer assembly of claim 5 wherein the verbal encouragement voice message sent is chosen from a plurality of verbal voice messages stored in the audio message storage unit; wherein at least one of the plurality of verbal encouragement voice messages is used where the measurement reading is lower than the target measurement and at least one of the plurality of verbal encouragement voice messages is used where the measurement reading is higher than the target measurement; wherein the plurality of verbal voice messages allow an appropriate verbal voice message to be selected according to the user's measurement performance of the sustained maximal inspiration (SMI) procedure.

7. The Incentive Spirometer assembly of claim 6 wherein the plurality of verbal voice messages use a humanlike voice.

8. The Incentive Spirometer assembly of claim 4 wherein when retrieving data regarding a user's use of the Incentive Spirometer device said Incentive Spirometer device is removably secured to said base station.

9. The Incentive Spirometer assembly of claim 4 wherein said base station is in electronic or wireless communication with a microprocessor-based device, wherein data retrieved through said base station can be downloaded and saved to the microprocessor-based device.

* * * * *